(12) United States Patent
Luo et al.

(10) Patent No.: US 10,420,878 B2
(45) Date of Patent: Sep. 24, 2019

(54) SYRINGE ASSEMBLY

(71) Applicant: Guangdong Haiou Medical Apparatus Co., Ltd., Puning (CN)

(72) Inventors: Shaoji Luo, Puning (CN); Zhuoxuan Zhang, Puning (CN)

(73) Assignee: Guangdong Haiou Medical Apparatus Co., Ltd., Puning (CN)

( * ) Notice: Subject to any disclaimer, the term of this patent is extended or adjusted under 35 U.S.C. 154(b) by 224 days.

(21) Appl. No.: 15/314,598

(22) PCT Filed: Nov. 19, 2015

(86) PCT No.: PCT/CN2015/094978
§ 371 (c)(1),
(2) Date: Nov. 29, 2016

(87) PCT Pub. No.: WO2017/084057
PCT Pub. Date: May 26, 2017

(65) Prior Publication Data
US 2017/0281853 A1    Oct. 5, 2017

(51) Int. Cl.
*A61M 5/50* (2006.01)
*A61M 5/00* (2006.01)
(Continued)

(52) U.S. Cl.
CPC ............ *A61M 5/002* (2013.01); *A61M 5/178* (2013.01); *A61M 5/315* (2013.01);
(Continued)

(58) Field of Classification Search
CPC .... A61M 2005/3117; A61M 2005/323; A61M 5/178; A61M 5/3205; A61M 5/3234;
(Continued)

(56) References Cited

U.S. PATENT DOCUMENTS 6,706,019 B1    3/2004    Parker

FOREIGN PATENT DOCUMENTS

CN    101284154 A    10/2008
CN    201375735 Y    1/2010
(Continued)

OTHER PUBLICATIONS

International Search Report for PCT/CN2015/094978.

*Primary Examiner* — Deanna K Hall

(57) ABSTRACT

A syringe assembly includes a plunger assembly, a syringe body, and a needle. The plunger assembly includes a plunger rod, a spring, a plunger base, and a plunger plug. The plunger rod includes a first end member having a first stepped part positioned in an inner wall thereof, a second end member, and a first accommodating room. The plunger base includes a plunger body, a projection, a second stepped part, a plunger member, and a locating member. The plunger body is received in the first accommodating room, and the projection abuts against the first end member. The spring is arranged around the plunger body and positioned between the first stepped part and the second stepped part. The plunger plug is mounted to the second end member, and defines a fixing groove. The syringe body includes a needle cannula, a needle base, a fixing pole, and a fixing valve. The plunger assembly is received in the needle cannula. The needle base is mounted to the needle cannula. The fixing valve is received in the needle base. The fixing pole is received in the fixing valve and protrudes out of the needle base. The needle is received in the fixing pole. The syringe assembly of the present invention is prevented from reuse and accidently damage because the needle can retract into the plunger rod using restoring force of the spring.

14 Claims, 12 Drawing Sheets

(51) Int. Cl.
  *A61M 5/178* (2006.01)
  *A61M 5/315* (2006.01)
  *A61M 5/32* (2006.01)
  *A61M 5/31* (2006.01)

(52) U.S. Cl.
  CPC ............ *A61M 5/3234* (2013.01); *A61M 5/50* (2013.01); *A61M 5/3205* (2013.01); *A61M 2005/3117* (2013.01); *A61M 2005/323* (2013.01); *A61M 2005/3241* (2013.01)

(58) Field of Classification Search
  CPC .. A61M 5/50; A61M 5/5066; A61M 5/31501; A61M 5/5013
  See application file for complete search history.

(56) References Cited

FOREIGN PATENT DOCUMENTS

| | | | |
|---|---|---|---|
| CN | 201701572 U | | 1/2011 |
| CN | 102188766 A | | 9/2011 |
| CN | 103239782 A | | 8/2013 |
| CN | 103721325 | * | 4/2014 |
| CN | 103721325 A | | 4/2014 |
| CN | 204655699 U | | 9/2015 |

\* cited by examiner

SYRINGE ASSEMBLY

BACKGROUND

1. Technical Field

The present disclosure generally relates to a syringe assembly.

2. Description of Related Art

Single-use syringes are well known in the medical arts in order to inject medicinal liquid or draw blood. A single-use syringe prevents reuse of the syringe to minimize exposure of patients to HIV, hepatitis and other blood pathogens. But a traditional single-use syringe is well-kept after use, so that the traditional single-use syringe can be reused by offenders, resulting in increasing risks of infection. In addition, a needle of traditional single-use syringe after use is exposed to an outside, so that the needle easily scratches the skin to lead to new infections, and recycling is cumbersome.

SUMMARY

The disclosure relates to a syringe assembly.

In one aspect, a syringe assembly includes a syringe body, a plunger assembly, and a needle. The plunger assembly includes a plunger rod, a spring, a plunger base, and a plunger plug, the plunger rod having a first end member, a second end member, and a first accommodating room, the first end having a first stepped part positioned in an inner wall thereof. The plunger base includes a plunger body, a locating member, a plunger member positioned at a distal end of the plunger body, a second stepped part protruding from an outer circumference of the plunger body and adjacent to the plunger member, and a projection protruding from an outer circumference of the plunger body and adjacent to the locating member. The plunger body is partly received in the first accommodating room together with the projection abutting against a top portion of the first end member, and the spring is arranged around the plunger body and located between the first stepped part and the second stepped part, and wherein the plunger plug is mounted to the second end member, and defines a fixing groove. The syringe body includes a needle cannula defining a second accommodating room to receiving the plunger assembly, a needle base mounted to the needle cannula and defining a first receiving groove, a fixing valve partly received in the first receiving groove and defining a second receiving groove, and a fixing pole partly received in the second receiving groove and protruding out of the first receiving groove. The fixing pole includes a first convex portion and a third receiving groove. The needle is mounted in the third receiving groove. When the syringe assembly is in an advanced position, the spring is in a compressed state, and the first convex portion abuts against the locating member, when the syringe assembly is in a destroyed position, the spring is in a free state, the fixing pole and the needle retracts into the first accommodating room of the plunger rod, and the plunger member is received in the fixing groove.

Wherein the plunger assembly comprises a hollow sealing plug, and the sealing plug is mounted to the first end member of the plunger rod and is received in the second accommodating room.

Wherein sealing plug defines a first locating groove, a second locating groove in communication with the first locating groove, and a first locating step located between the first locating groove and the second locating groove, wherein the first locating step, the first locating groove and the second locating groove are located in an inner wall of the sealing plug; the first end member includes a first locating protrusion, a second locating protrusion, and a first slot located between the first locating protrusion and the second locating protrusion; wherein the first locating step is received in the first slot, the first locating protrusion is received in the first locating groove, and a top portion of the second locating protrusion abuts against a bottom portion of the second locating groove.

Wherein the sealing plug includes a third locating protrusion away from second locating groove, and a fourth locating protrusion adjacent to the first locating groove, wherein the third locating protrusion and the fourth locating protrusion are located in outer wall of the sealing plug, and wherein the third locating protrusion and the fourth locating protrusion engage with an inner wall of the second accommodating room in a sealing state to seal the needle cannula and the plunger assembly.

Wherein the fixing valve includes a pair of locating arms, and each of the locating arms has a hook located in a distal end thereof, and wherein the hooks catch a distal end of the fixing pole to prevent the fixing pole from disengaging from the fixing valve.

Wherein each of the locating arms is a cantilever.

Wherein the first receiving groove comprises a first channel and a second channel in communication with the first channel, wherein a diameter of the first channel is greater than a diameter of the second channel, and the fixing valve is received in the first channel.

Wherein the needle base comprises a second convex portion located in an inner wall of the first receiving groove and between the first channel and the second channel, wherein the fixing pole comprises a third stepped part, and the second convex portion abuts against the third stepped part.

Wherein the syringe body comprises a sealing ring mounted between the needle base and the fixing pole to seal the needle and the fixing pole.

Wherein the plunger base comprises a head portion located in another distal end thereof and adjacent to the locating member.

Wherein the third receiving groove comprises a third channel and a fourth channel in communication with the third channel, wherein a diameter of the third channel is greater than a diameter of the fourth channel, and wherein the head portion is received in the third channel, and the needle is fixed in the fourth channel.

Wherein a connecting portion is arranged between the third channel and the fourth channel, and the connecting portion defines a through hole.

Wherein the plunger member defines a first groove, and the head portion defines a second groove.

Wherein the plunger body defines a third groove adjacent to the projection.

BRIEF DESCRIPTION OF THE DRAWINGS

In order to more clearly illustrate the technical scheme of the present invention, the drawings used in the following embodiments are briefly introduced. Obviously, the following described drawings are only drawing of some embodiments of the present invention, it is obvious to a person of ordinary skill in the art to get other drawings from these drawings.

DETAILED DESCRIPTION

Figure 1:
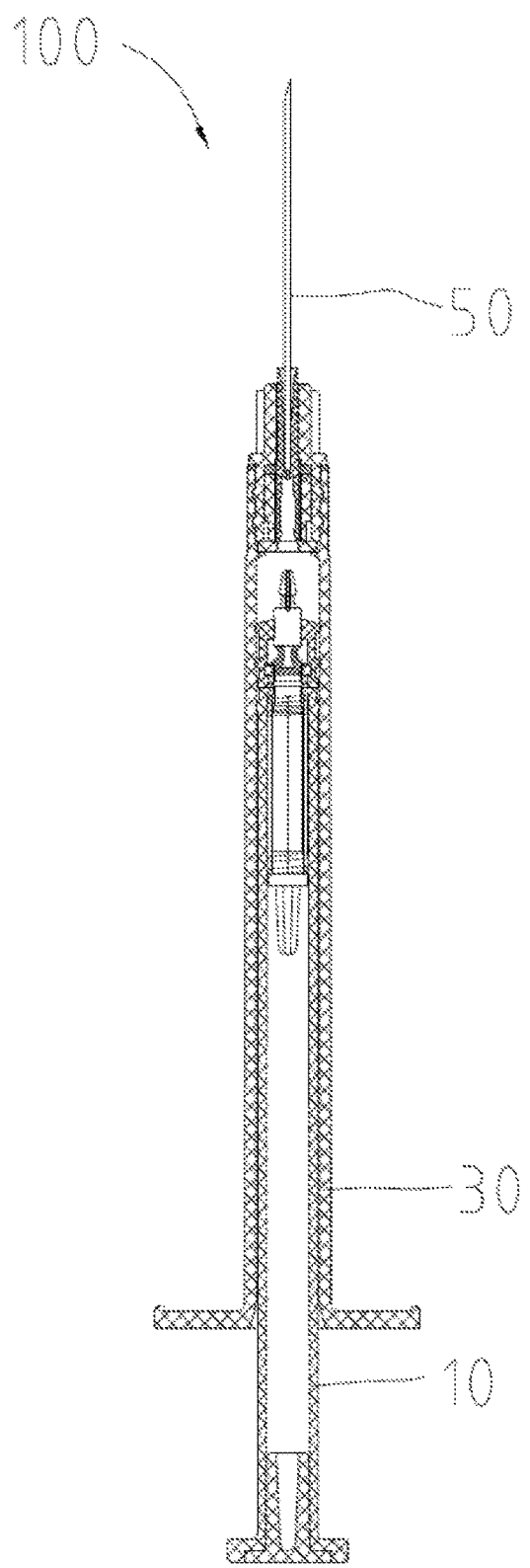
FIG. 1 is a cross-sectional view of a syringe assembly in accordance with the present invention.
Figure 2:
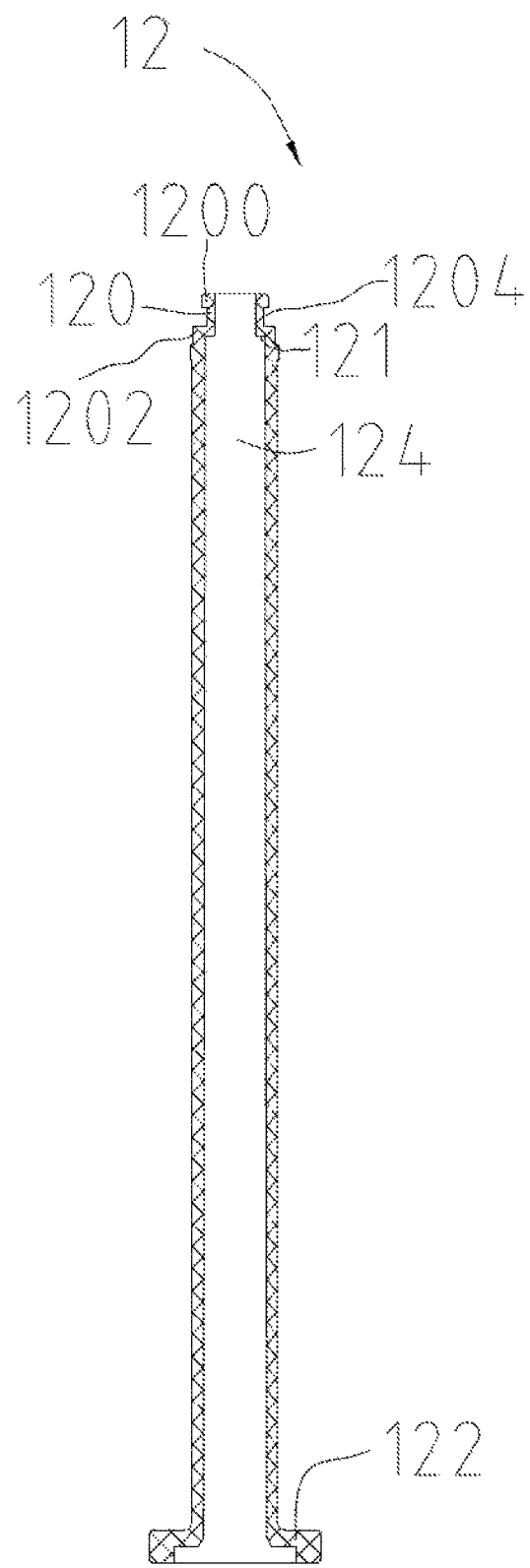
FIG. 2 is a cross-sectional view of a plunger rod of the syringe assembly of FIG. 1.

The disclosure is illustrated by way of example and not by way of limitation in the figures of the accompanying drawings, in which like reference numerals indicate similar elements. The embodiments described in accordance with the drawings are only examples, and thus the claimed invention is not limited thereto.

Referring to FIG. 1, a syringe assembly 100 of the present invention includes a syringe body 30, a plunger assembly 10 mounted to the syringe body 30, and a needle 50 mounted to the syringe body 30.

Referring to FIG. 1 to FIG. 12, the plunger assembly 10 includes a plunger rod 12, a spring 14, a plunger base 16, and a plunger plug 18. The plunger rod 12 includes a first end member 120, a second end member 122, and a first accommodating room 124, wherein the first end member 120 includes a first stepped part 121 located in an inner wall thereof. The plunger base 16 includes a plunger body 160, a projection 162, a second stepped part 164, a plunger member 166, and a locating member 168. The projection 162 protrudes from an outer circumference of the plunger body 160 and is adjacent to the locating member 168. The plunger member 166 is positioned at a distal end of the plunger body 160, and the second stepped part 164 protrudes from an outer circumference of the plunger body 160 and is adjacent to the plunger member 166. The plunger body 160 is partly received in the first accommodating room 124 together with the projection 162 abutting against a top portion of the first end member 120, and the spring 14 is arranged around the plunger body 160 and located between the first stepped part 121 and the second stepped part 164. The plunger plug 18 is mounted to the second end member 122, and defines a fixing groove 180. The syringe body 30 includes a needle cannula 32, a needle base 34, a fixing pole 36, and a fixing valve 38. The second needle cannula 32 defines a second accommodating room 320 to receiving the plunger assembly 10. The needle base 34 is mounted to the needle cannula 32 and defines a first receiving groove 340. The fixing valve 38 is partly received in the first receiving groove 340 and defines a second receiving groove 380. The fixing pole 36 is partly received in the second receiving groove 380 and protrudes out of the first receiving groove 340, and includes a first convex portion 362 and a third receiving groove 360. The needle 50 is mounted in the third receiving groove 360. When the syringe assembly 100 is in an advanced position, the spring 14 is in a compressed state, and the first convex portion 362 abuts against the locating member 168; when the syringe assembly 100 is in a destroyed position, the spring 14 is in a free state, the fixing pole 36 and the needle 50 retracts into the first accommodating room 124 of the plunger rod 12, and the plunger member 166 is received in the fixing groove 180.

In one embodiment, the plunger member 166 defines a first groove 1660, the plunger member 166 deforms toward a centre line of the first groove 1660 during the plunger member 166 being received in the fixing groove 180, i.e., the plunger member 166 deforms inwardly, so that the plunger member 166 is easily received in the fixing groove 180, thereby improving the convenience of use.

In use, the syringe assembly 100 injects a patient with medicinal liquid, the plunger rod 12 is actuated to advance the syringe assembly 100 from a retracted position (referring to FIG. 9) to the advanced position (referring to FIG. 10) and drives the spring 14 to be compressed, the plunger base 16 is advanced as the medicinal liquid within the second accommodating room 320 is forced from the second accommodating room 320 through needle 50. In the advanced position, the projection 162 abuts against the first end member 120, the first convex portion 362 abuts against the locating member 168; After injection, the plunger rod 12 is continuously pushed, the projection 162 disengages from the first end member 120 and the projection 162 deforms toward a centre line of the plunger body 160 because the plunger base 16 is further pressed, and the spring 14 moves from the compressed state to the free state and drives the plunger base 16 together with the fixing pole 36 and needle 50 to retract into the first accommodating room 120 of the plunger rod 12, so that the syringe assembly 100 moves from the advanced position to the destroyed position, thereby preventing reuse of the syringe assembly 100, accidental injury and the risks of infection. That is to say, the restoring force of the spring 14 automatically drives the plunger base 16, the fixing pole 36 and needle 50 to retract into the first accommodating room 120 of the plunger rod 12. In the destroyed position, the plunger member 166 is received in the fixing groove 180.

Furthermore, the plunger member 166 is received in the fixing groove 180 so that the plunger base 16 is fixed in the plunger plug 18.

Figure 3:
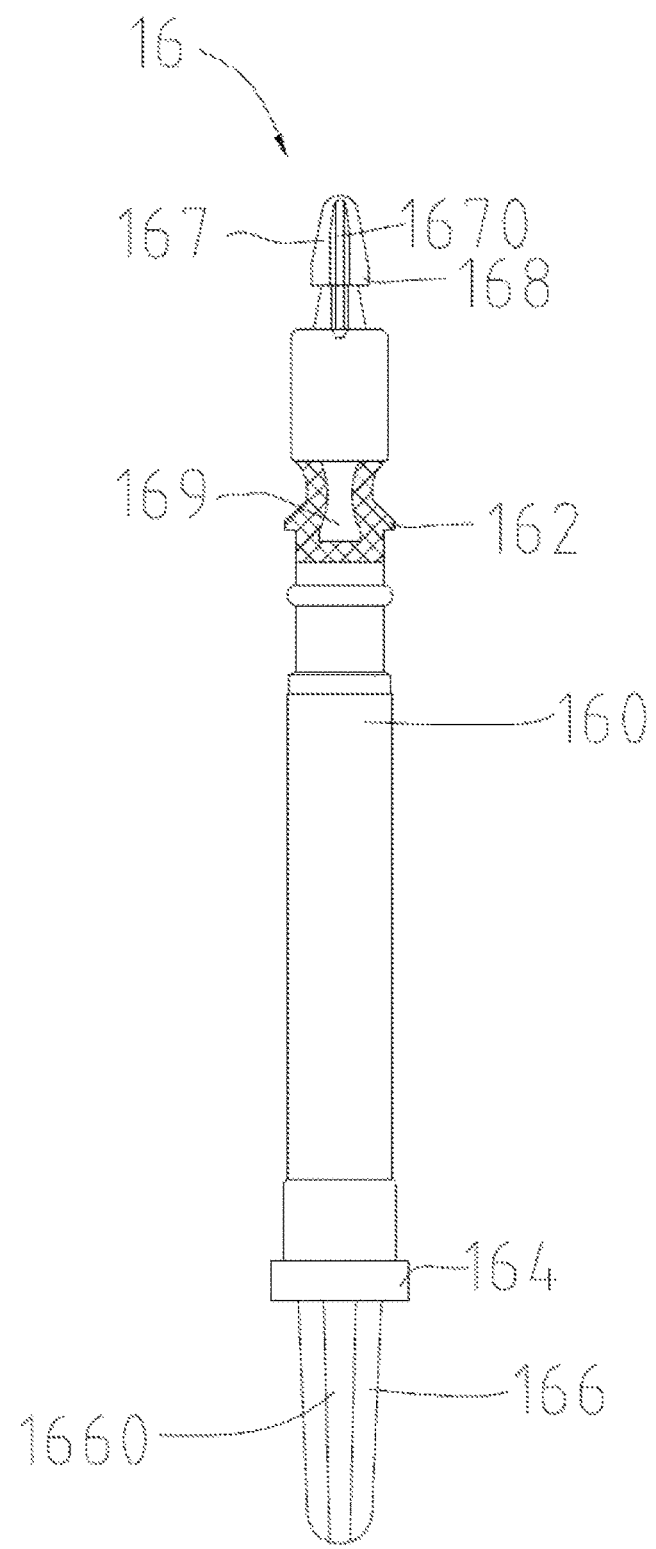
FIG. 3 is a plan view of a plunger base of the syringe assembly of FIG. 1.
Figure 4:
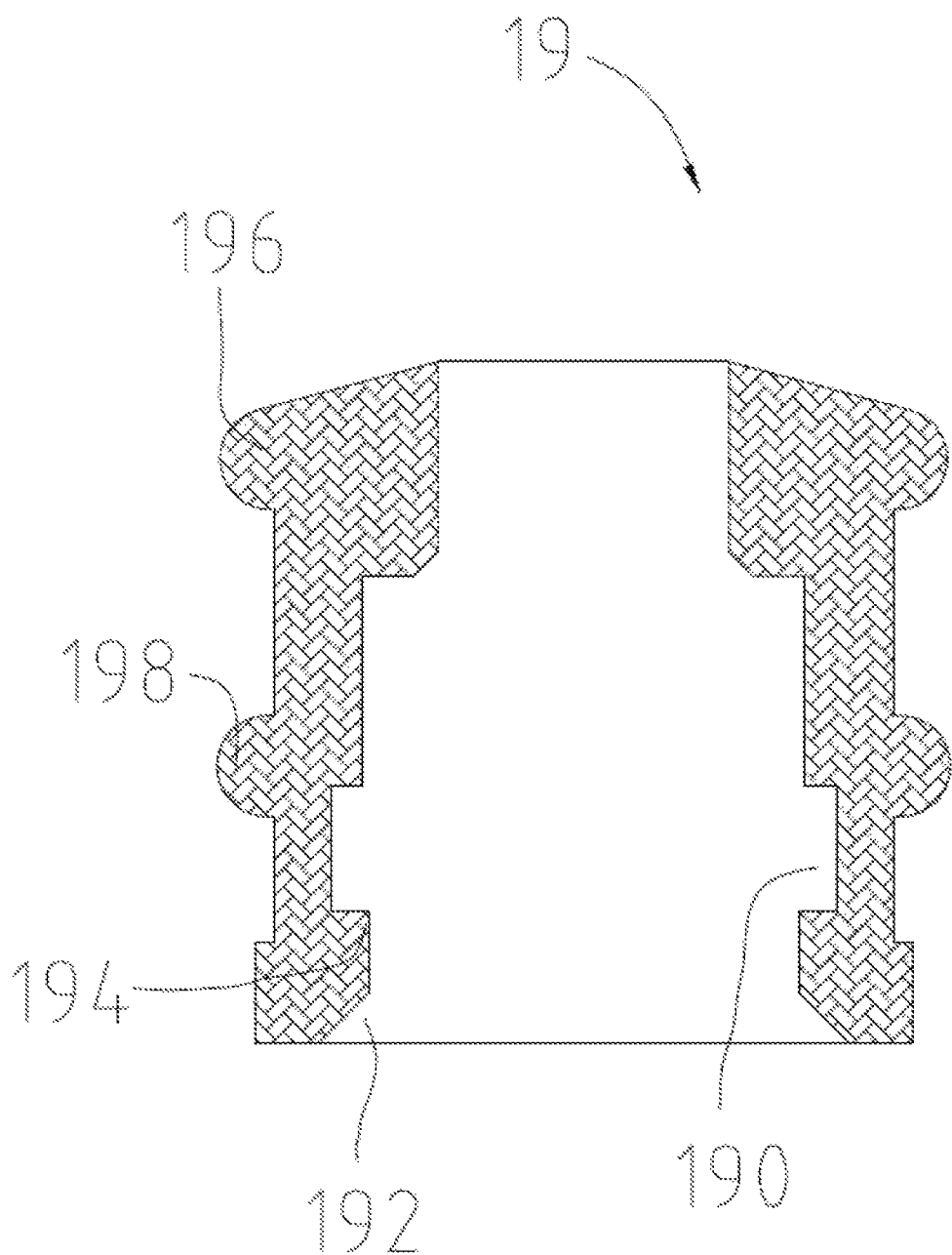
FIG. 4 is a cross-sectional view of a sealing plug of the syringe assembly of FIG. 1.
Figure 11:
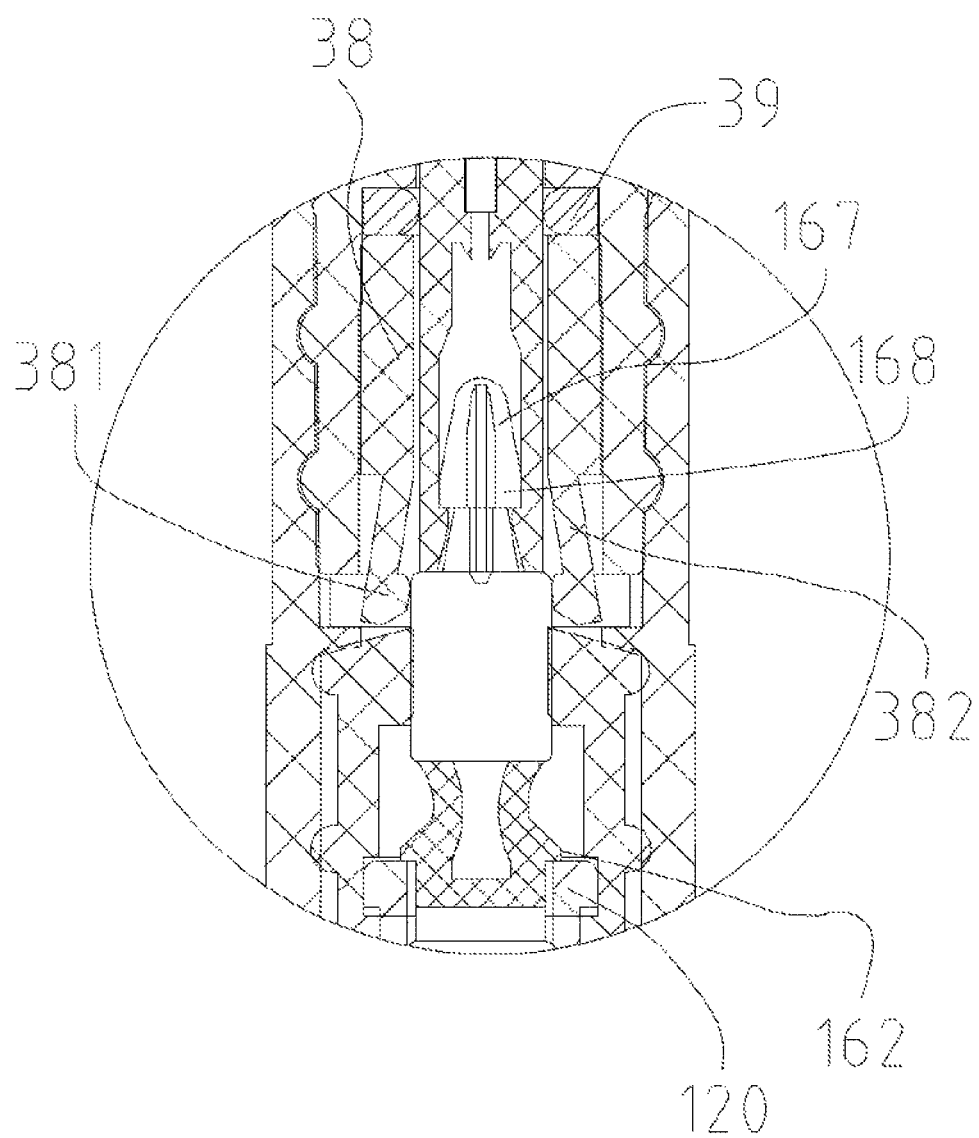
FIG. 11 is an enlarged view of a circle portion XI of FIG. 10.
Figure 12:
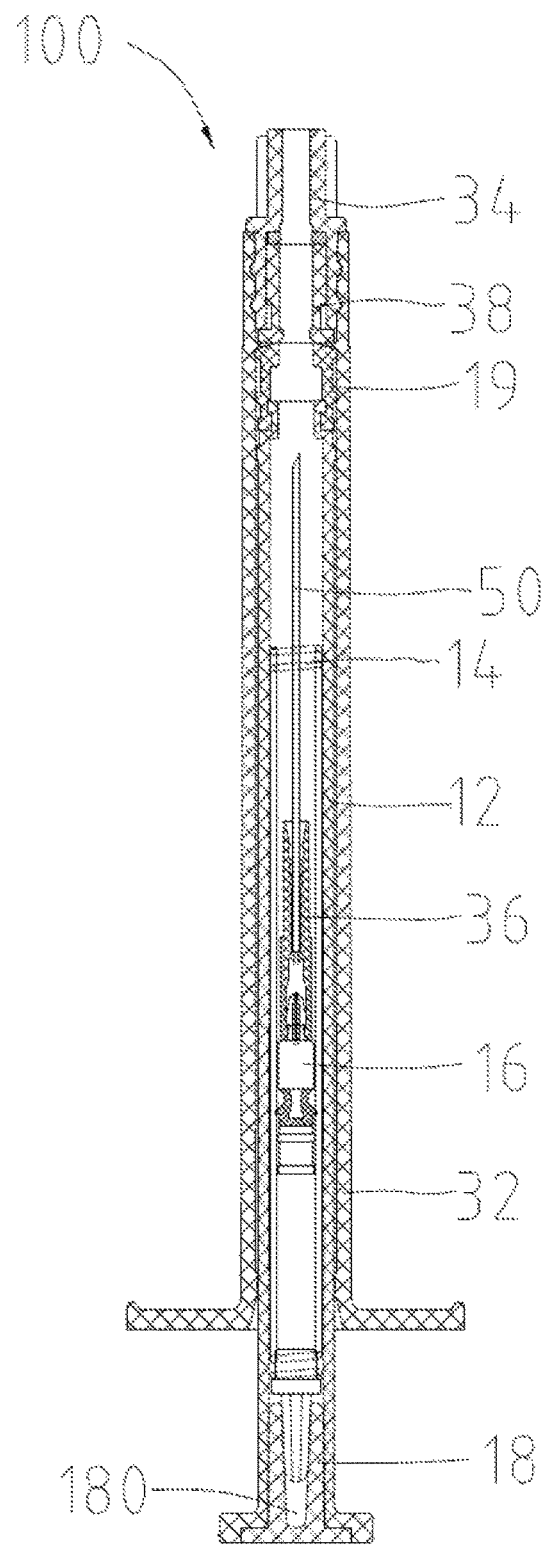
FIG. 12 is similar to FIG. 10, but showing the syringe assembly in a destroyed position.

Referring to FIG. 3, FIG. 11, and FIG. 12, the plunger body 160 defines a third groove 169 adjacent to the projection 162. When the plunger base 16 is pressed, the plunger body 160 deforms toward the third groove 169, i.e., the plunger body 160 deforms inwardly, so that the projection 162 deforms toward a centre line of the plunger body 160, thereby the plunger base 16 and the needle 50 retract into the first accommodating room 124 of the plunger rod 12 under the action of the restoring force of the spring 14.

Referring to FIG. 1, FIG. 2, and FIGS. 4-5, the plunger assembly 10 includes a hollow sealing plug 19. The sealing plug 19 is mounted to the first end member 120 of the plunger rod 12 and is received in the second accommodating room 320, when the syringe assembly 100 moves from the compressed state to the retracted position, the sealing plug 19 slidably fit with an inner wall of the second accommodating room 320. The sealing plug 19 defines a first locating groove 190, a second locating groove 192 in communication with the first locating groove 190, and a first locating step 194 located between the first locating groove 190 and the second locating groove 192, wherein the first locating step 194, the first locating groove 190 and the second locating groove 192 are located in an inner wall of the sealing plug 19. The first end member 120 includes a first locating protrusion 1200, a second locating protrusion 1202, and a first slot 1204 located between the first locating protrusion 1200 and the second locating protrusion 1202. The first locating step 194 is received in the first slot 1204, the first locating protrusion 1200 is received in the first locating groove 190, and a top portion of the second locating protrusion 1202 abuts against a bottom portion of the second locating groove 192. The sealing plug 19 includes a third locating protrusion 196 away from second locating groove 192, and a fourth locating protrusion 198 adjacent to the first locating groove 190, wherein the third locating protrusion 196 and the fourth locating protrusion 198 are located in outer wall of the sealing plug 19. The third locating protrusion 196 and the fourth locating protrusion 198 engage an inner wall of the second accommodating room 320 in a sealing state to seal the needle cannula 32 and the plunger assembly 10.

The sealing plug 19 is located between the needle cannula 32 and the plunger assembly 10, thereby there is no leakage phenomenon when the syringe assembly 100 sucks or injects the medicinal liquid.

Figure 8:
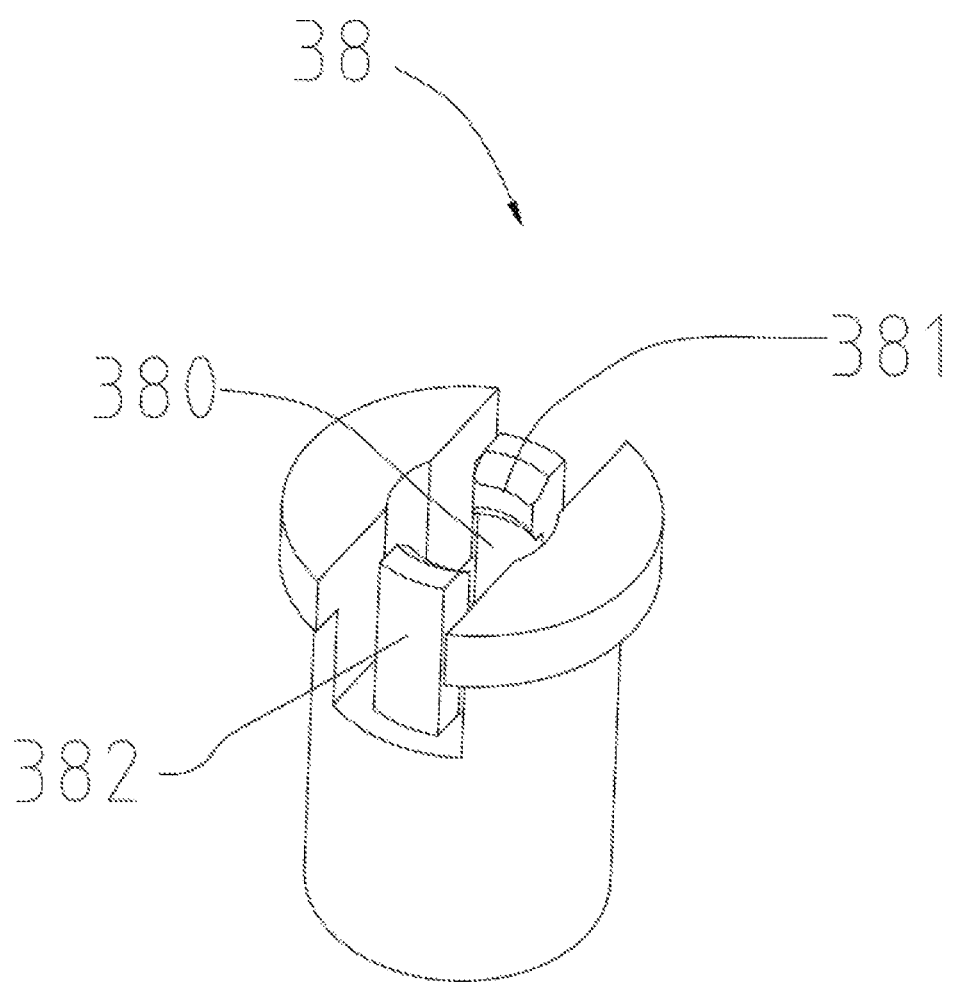
FIG. 8 is a cross-sectional view of a fixing valve of the syringe assembly of FIG. 1.
Figure 9:
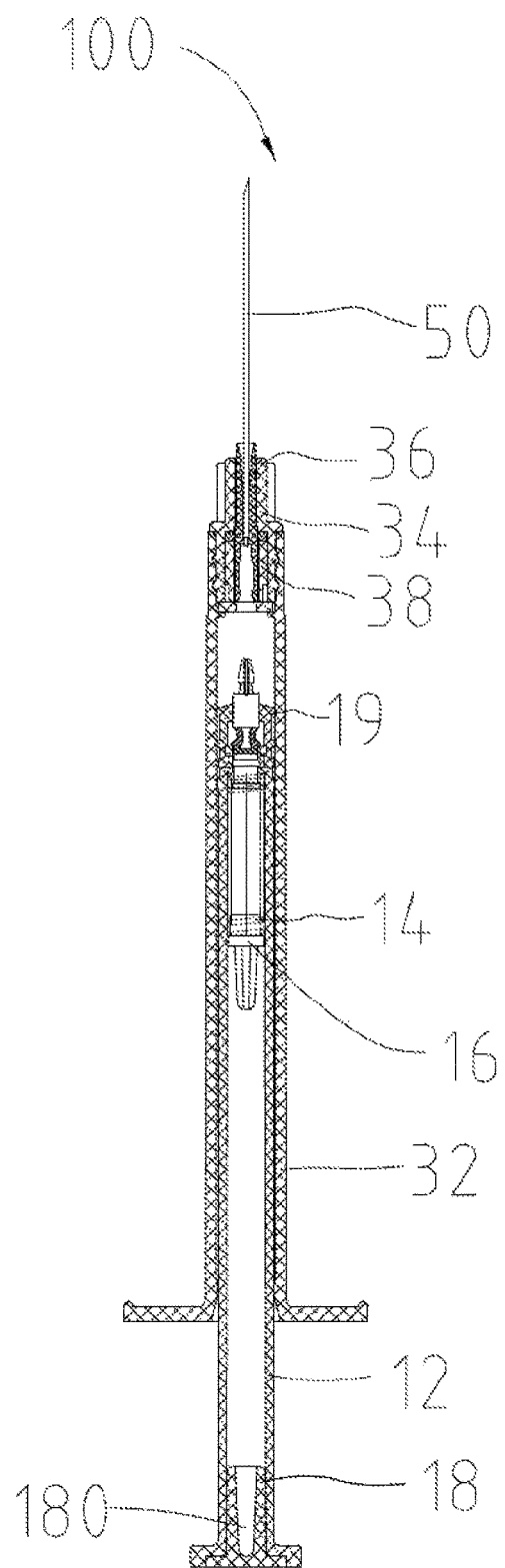
FIG. 9 is similar to FIG. 1, showing the syringe assembly in a retracted position.

Referring to FIG. 3 and FIG. 8, the fixing valve 38 includes a pair of locating arms 382, and each of the locating arms 382 has a hook 381 located in a distal end thereof. The hooks 381 catch a distal end of the fixing pole 36 to prevent the fixing pole 36 from disengaging from the fixing valve 38. Each of the locating arms 382 is a cantilever and flexible.

The plunger base 16 includes a head portion 167 located in another distal end thereof and adjacent to the locating member 168. In one embodiment, the head portion 167 has a bullet shape. When the syringe assembly 100 injects the patient with medicinal liquid, the head portion 167 opens the locating arms 382 and inserts into the third receiving groove 360 of the fixing pole 36.

The head portion 167 defines a second groove 1670 along a longitudinal axis thereof. During the head portion 167 inserting into the third receiving groove 360, the head portion 167 deforms toward a centre line of the third receiving groove 360, i.e. the head portion 167 deforms inwardly, thereby the head portion 167 easily extends through the locating arms 382 and inserts into the third receiving groove 360, resulting in improving the convenience of use.

Because each of the locating arms 382 is a cantilever and has flexibility, the head portion 167 easily extends through the locating arms 382 and inserts into the third receiving groove 360, resulting in improving the convenience of use.

In one embodiment, a maximum diameter of the head portion 167 is equal to a diameter of the locating member 168. A neck member is arranged between the locating member 168 and the plunger body 160, a diameter of the neck member is smaller than the diameter of the locating member 168 or a diameter of the plunger body 160.

Figure 6:
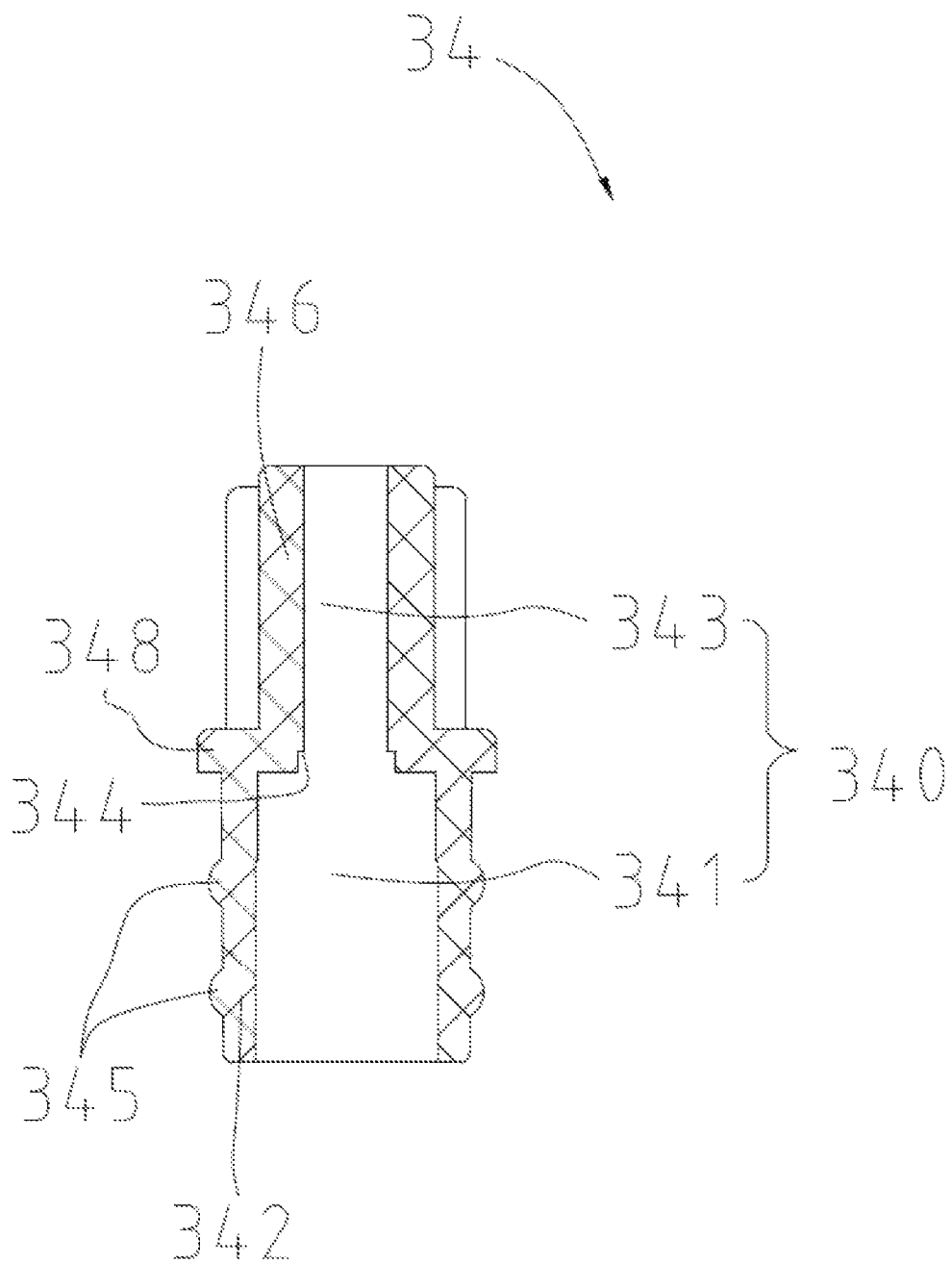
FIG. 6 is a cross-sectional view of a needle base of the syringe assembly of FIG. 1.

Referring to FIG. 6 and FIG. 8, the first receiving groove 340 includes a first channel 341 and a second channel 343 in communication with the first channel 341. A diameter of the first channel 341 is greater than a diameter of the second channel 343. The fixing valve 38 is received in the first channel 341. The needle base 34 includes a second convex portion 344 located in an inner wall of the first receiving groove 340 and between the first channel 341 and the second channel 343. The fixing pole 36 includes a third stepped part 364, and the second convex portion 344 abuts against the third stepped part 364.

When plunger rod 12 is actuated to inject the medicinal liquid to the patient, the fixing pole 36 cannot accidentally disengage from the needle base 34 because the second convex portion 344 abuts against the third stepped part 364.

Figure 7:
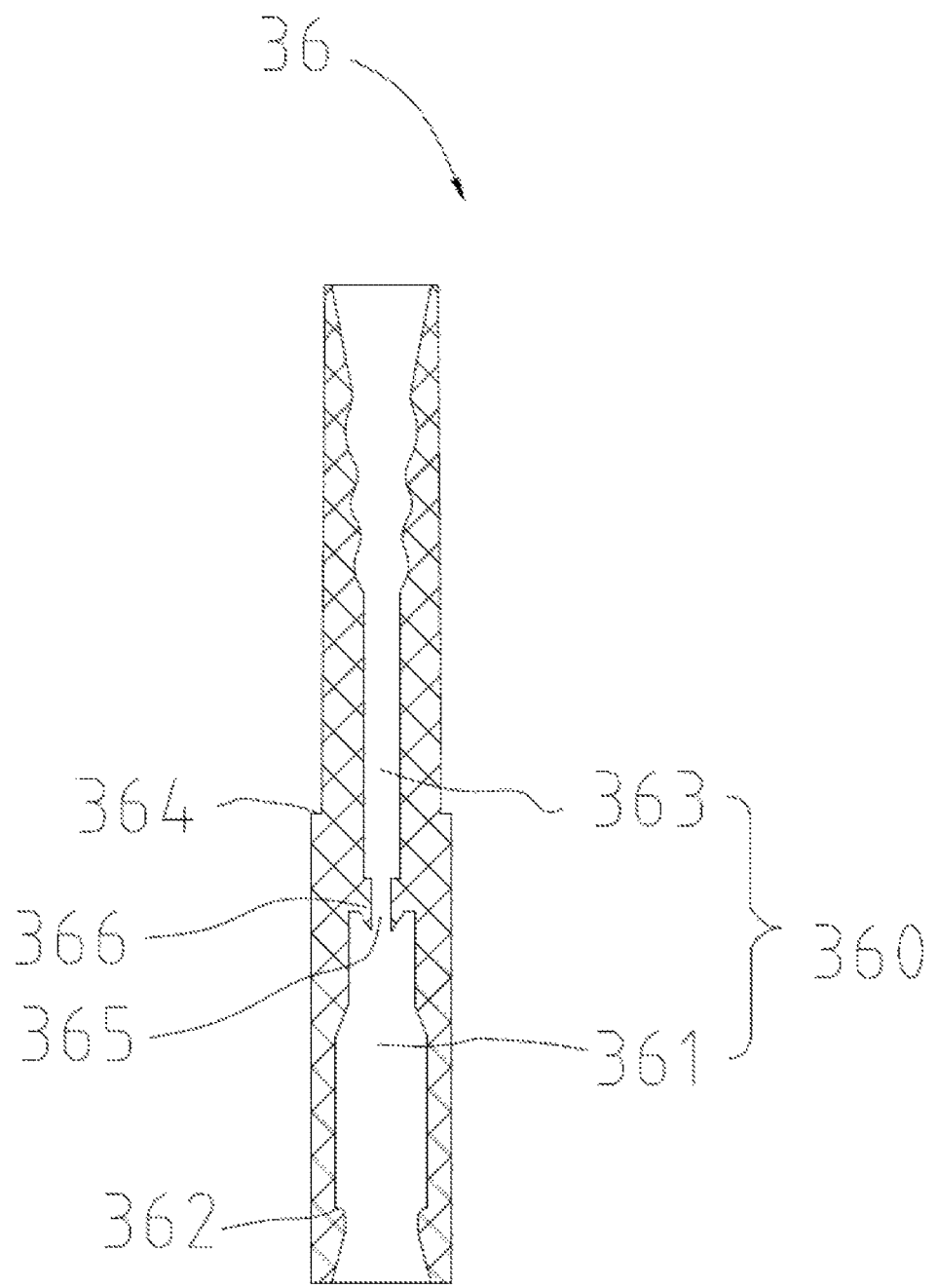
FIG. 7 is a cross-sectional view of a fixing pole of the syringe assembly of FIG. 1.

Referring to FIG. 1 and FIG. 7, the third receiving groove 360 includes a third channel 361 and a fourth channel 363 in communication with the third channel 361. A diameter of the third channel 361 is greater than a diameter of the fourth channel 363. The head portion 167 is received in the third channel 361, and the needle 50 is fixed in the fourth channel 363. A connecting portion 366 is arranged between the third channel 361 and the fourth channel 363, and the connecting portion 366 defines a through hole 365 to facilitate the medicinal liquid to flow into the needle 50.

Figure 10:
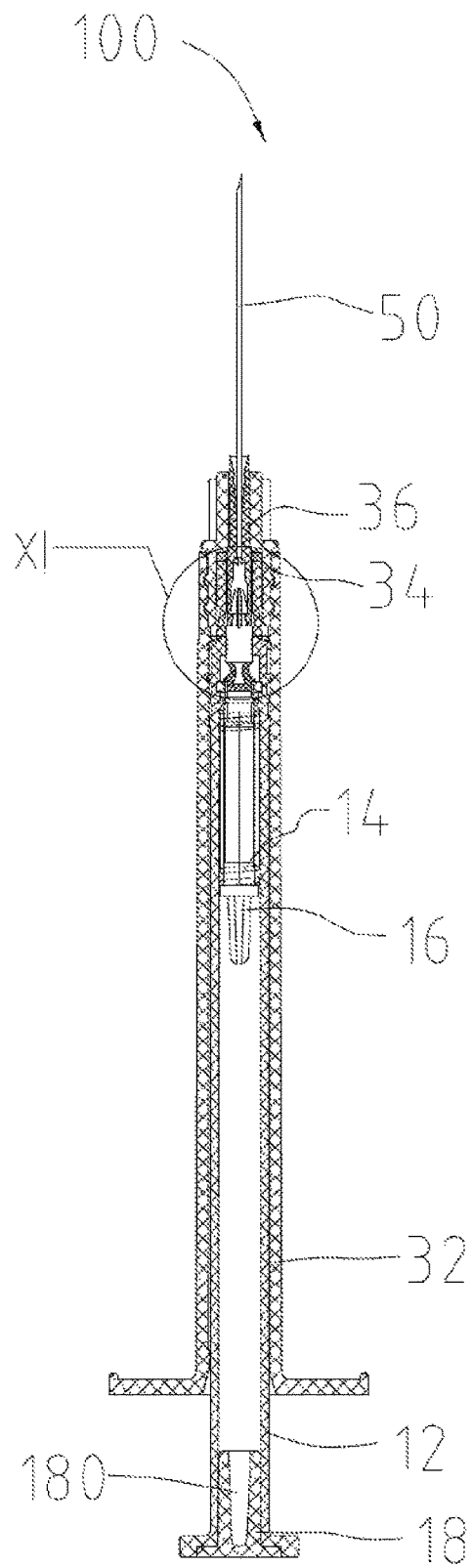
FIG. 10 is similar to FIG. 9, but showing the syringe assembly in an advanced position.

Referring to FIG. 10 and FIG. 0.11, the syringe body 30 includes a sealing ring 39 mounted between the needle base 34 and the fixing pole 36 to seal the needle base 34 and the fixing pole 36.

Figure 5:
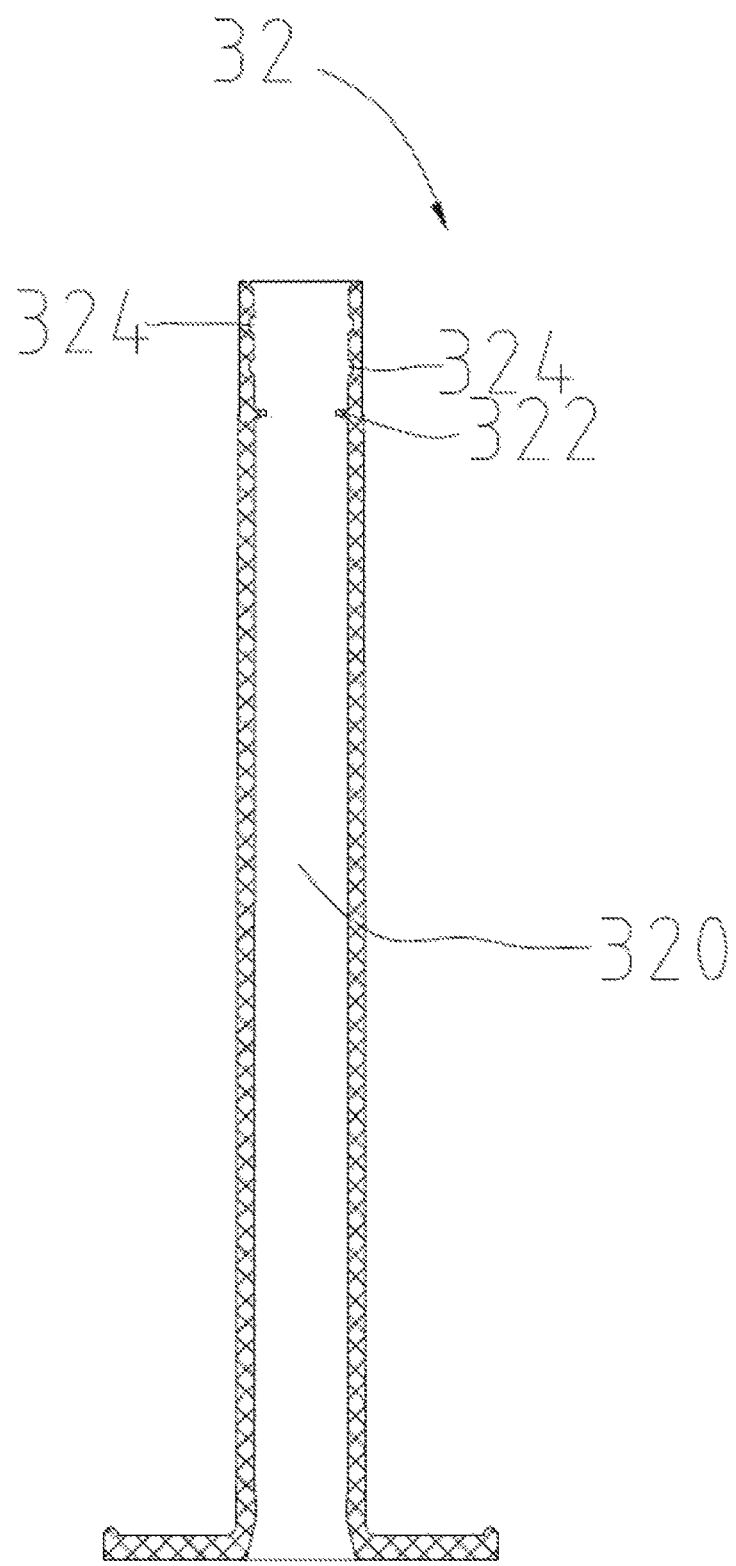
FIG. 5 is a cross-sectional view of a needle cannula of the syringe assembly of FIG. 1.

Referring to FIG. 5 and FIG. 6, the needle cannula 32 includes a first holding protrusion 322 and a plurality of holding slots 324. The needle base 34 includes a receiving space 342, a holding portion 346, and a second holding protrusion 348 located between the receiving space 342 and the holding portion 346. The first receiving groove 340 extends through the receiving space 342 and the holding portion 346. The first channel 341 is positioned in the receiving space 342, and the second channel 343 is positioned in the holding portion 346. An outer wall of the receiving space 342 includes a plurality of locating discs 345 corresponding to the holding slots 324. In assembly, a bottom portion of the receiving space 342 abuts against the first holding protrusion 322 of the needle cannula 32, the locating discs 345 are received in the holding slots 324 respectively, the second holding protrusion 348 abuts against a top portion of the needle cannula 32, thus the needle base 34 is mounted to the needle cannula 32.

Referring to FIG. 1 to FIG. 8, in assembly, the spring 14 is mounted around the plunger base 16, the plunger base 16 is inserted into the first accommodating room 124 together with the plunger body 160 being partly received in the first accommodating room 124, the projection 162 abuts against the top portion of the first end member 120 of the plunger rod 12 with the spring 14 being positioned between the first stepped part 121 of the plunger rod 12 and the second stepped part 164 of the plunger base 16, the sealing plug 19 is mounted to the first end member 120 of the plunger rod 12, the first locating step 194 being received in the first slot 1204, the first locating protrusion 1200 is received in the first locating groove 190, and the top portion of the second locating protrusion 1202 abuts against the bottom portion of the second locating groove 192, thus the plunger rod 12, the sealing plug 19, the spring 14, and the plunger base 16 are mounted to the plunger assembly 10. The fixing valve 38 is received in the first channel 341 of the needle base 34, the fixing pole 36 is partly received in the second receiving groove 380 and protrudes out of the second channel 343, the receiving space 342 of the needle base 34 is received in the needle cannula 32, thus the needle 32, the needle base 34, the fixing pole 36 and the fixing valve 38 are mounted to the syringe body 30. The plunger assembly 10 is mounted to the needle cannula 32, the needle 50 is mounted to the fourth channel 363 of the fixing pole 36, thus the plunger assembly 10, the syringe body 30, and the needle 50 are mounted to the syringe assembly 100.

Referring to FIG. 1 to FIG. 12, when the syringe assembly 100 is in the retracted position, the syringe assembly 100 pulls the medical liquid or blood from the patient; when the syringe assembly 100 is in the advanced position, the syringe assembly 100 can inject the patient with the medical liquid, in the advanced position, the head portion 167 of the plunger base 16 opens the locating arms 382 of the fixing valve 38 and inserts into the third receiving groove 360 of the fixing pole 36 with the locating member 168 of the plunger rod 16 abutting against the first convex portion 362 of the fixing pole 36, and the spring 14 is compressed; after injection, the plunger rod 12 is continuously pushed, the projection 16 disengage from the first end member 120 and the deforms toward the centre line of the plunger body 160 because the plunger base 16 is further pressed, and the spring 14 moves from the compressed state to the free state and drives the plunger base 16 together with the fixing pole 36 and needle 50 to retract into the first accommodating room 120 of the plunger rod 12, so that the syringe assembly 100 moves from the advanced position to the destroyed position, thereby preventing reuse of the syringe assembly 100, accidental injury and the risks of infection.

Although the features and elements of the present disclosure are described as embodiments in particular combinations, each feature or element can be used alone or in other various combinations within the principles of the present disclosure to the full extent indicated by the broad general meaning of the terms in which the appended claims are expressed.

What is claimed is:

1. A syringe assembly, comprising:
   a plunger assembly comprising a plunger rod, a spring, a plunger base, and a plunge plug, the plunger rod having a first end member, a second end member and a first accommodating room, the first end having a first stepped part positioned in an inner wall thereof, the plunger base comprising a plunger body, a locating member, a plunger member positioned at a distal end of the plunger body, a second stepped part protruding from an outer circumference of the plunger body and adjacent to the plunger member, and a projection protruding from an outer circumference of the plunger body and adjacent to the locating member; wherein the plunger body is partly received in the first accommodating room together with the projection abutting against a top portion of the first end member, and the spring is arranged around the plunger body and located between the first stepped part and the second stepped part, and wherein the plunger plug is mounted to the second end member and defines a fixing groove;
   a syringe body comprising a needle cannula defining a second accommodating room to receiving the plunger assembly, a needle base mounted to the needle cannula and defining a first receiving groove, a fixing valve partly received in the first receiving groove and defining a second receiving groove, and a fixing pole partly received in the second receiving groove and protruding out of the first receiving groove, the fixing pole comprising a first convex portion and a third receiving groove; and
   a needle mounted to the syringe body,
   wherein when the syringe assembly is in an advanced position, the spring is in a compressed state, and the first convex portion abuts against the locating member; when the syringe assembly is in a retracted position, the spring is in a free state, the fixing pole and the needle retract into the first accommodating room of the plunger rod, and the plunger member is received in the fixing groove.

2. The syringe assembly of claim 1, wherein the plunger assembly comprises a hollow sealing plug, and the sealing plug is mounted to the first end member of the plunger rod and is received in the second accommodating room, wherein when the syringe assembly moves from the compressed state to the retracted position, the sealing plug slidably fit with an inner wall of the second accommodating room.

3. The syringe assembly of claim 2, wherein the sealing plug defines a first locating groove, a second locating groove in communication with the first locating groove, and a first locating step located between the first locating groove and the second locating groove, wherein the first locating step, the first locating groove and the second locating groove are located in an inner wall of the sealing plug; the first end member includes a first locating protrusion, a second locating protrusion, and a first slot located between the first locating protrusion and the second locating protrusion; wherein the first locating step is received in the first slot, the first locating protrusion is received in the first locating groove, and a top portion of the second locating protrusion abuts against a bottom portion of the second locating groove.

4. The syringe assembly of claim 3, wherein the sealing plug includes a third locating protrusion away from second locating groove, and a fourth locating protrusion adjacent to the first locating groove, wherein the third locating protrusion and the fourth locating protrusion are located in outer wall of the sealing plug, and wherein the third locating protrusion and the fourth locating protrusion engage with an inner wall of the second accommodating room in a sealing state to seal the needle cannula and the plunger assembly.

5. The syringe assembly of claim 1, wherein the fixing valve includes a pair of locating arms, and each of the locating arms has a hook located in a distal end thereof and wherein the hooks catch a distal end of the fixing pole to prevent the fixing pole from disengaging from the fixing valve.

6. The syringe assembly of claim 5, wherein each of the locating arms is a cantilever and is resilient.

7. The syringe assembly of claim 1, wherein the first receiving groove comprises a first channel and a second channel in communication with the first channel, wherein a diameter of the first channel is greater than a diameter of the second channel, and the fixing valve is received in the first channel.

8. The syringe assembly of claim 7, wherein the needle base comprises a second convex portion located in an inner wall of the first receiving groove and between the first channel and the second channel, wherein the fixing pole comprises a third stepped part, and the second convex portion abuts against the third stepped part.

9. The syringe assembly of claim 1, wherein the syringe body comprises a sealing ring mounted between the needle base and the fixing pole to seal the needle and the fixing pole.

10. The syringe assembly of claim 1, wherein the plunger base comprises a head portion located in another distal end thereof and adjacent to the locating member.

11. The syringe assembly of claim 10, wherein the third receiving groove comprises a third channel and a fourth channel in communication with the third channel, wherein a diameter of the third channel is greater than a diameter of the fourth channel, and wherein the head portion is received in the third channel, and the needle is fixed in the fourth channel.

12. The syringe assembly of claim 11, wherein a connecting portion is arranged between the third channel and the fourth channel, and the connecting portion defines a through hole to facilitate a medicinal liquid to flow into the needle.

13. The syringe assembly of claim 10, wherein the plunger member defines a first groove to facilitate the plunger member to deform inwardly, and the head portion defines a second groove to facilitate the head portion to deform inwardly.

14. The syringe assembly of claim 11, wherein the plunger body defines a third groove adjacent to the projection to facilitate the plunger body to deform inwardly.

* * * * *